(12) United States Patent
Boger

(10) Patent No.: US 7,250,409 B2
(45) Date of Patent: Jul. 31, 2007

(54) NINGALIN B ANALOGS EMPLOYABLE FOR REVERSING MULTIDRUG RESISTANCE

(75) Inventor: Dale L. Boger, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 527 days.

(21) Appl. No.: 10/204,787

(22) PCT Filed: Mar. 1, 2001

(86) PCT No.: PCT/US01/06811

§ 371 (c)(1),
(2), (4) Date: Nov. 7, 2002

(87) PCT Pub. No.: WO01/64635

PCT Pub. Date: Sep. 7, 2001

(65) Prior Publication Data

US 2003/0220320 A1 Nov. 27, 2003

Related U.S. Application Data

(60) Provisional application No. 60/186,106, filed on Mar. 1, 2000.

(51) Int. Cl.
*A61P 43/00* (2006.01)
*A61K 31/40* (2006.01)
*A61K 31/55* (2006.01)
*C07D 207/00* (2006.01)
*C07D 223/14* (2006.01)

(52) U.S. Cl. ............ 514/214.01; 514/247; 514/411; 514/423; 540/576; 544/224; 548/430; 548/533

(58) Field of Classification Search .......... 514/214.01, 514/247, 411, 423; 540/576; 544/224; 548/430, 548/533
See application file for complete search history.

(56) References Cited

OTHER PUBLICATIONS

Boger, et al., "Thermal Cycloaddition of Dimethyl 1,2,4,5-Tetrazine-3,6-dicarboxylate with Electron-Rich Olefins: 1,2-Diazine and Pyrrole Introduction. Preparation of Octamethylporphin (OMP)", *J. Org. Chem. 49*: 4405-4409 (1984).
Boger, et al., "A Detailed, Convenient Preparation of Dimethyl 1,2,4,5-Tetrazine-3,6-dicarboxylate", *J. Org. Chem. 50*: 5377-5379 (1985).
Boger, et al., "Total Synthesis of Prodigiosin, Prodigiosene, and Desmethoxyprodigiosin: Diels-Alder Reactions of Heterocyclic Azadienes and Development of an Effective Palladium(II)-Promoted 2,2'-Bipyrrole Coupling Procedure", *J. Org. Chem. 53*: 1405-1415 (1988).
Lindquist, et al., "New Alkaloids of the Lamellarin Class from the Marine Ascidian *Didemnum chartaceum* (Sluiter, 1909)", *J. Org. Chem. 53*: 4570-4574 (1988).
Boger, et al., "*d,l*- and *meso*-Isochrysohermidin: Total Synthesis and Interstrand DNA Cross-Linking", *J. Am. Chem. Soc. 115*: 11418-11425 (1993).
Fürstner, et al., "A New, Titanium-Mediated Approach to Pyrroles: First Synthesis of Lukianol A and Lamellarin O Dimethyl Ether", *J. Org. Chem. 60*: 6637-6641 (1995).
Terpin, et al., "Biomimetic Total Synthesis of Polycitrin A", *Tetrahedron 51*: 9941-9946 (1995).
Quesada, et al., "Polyaromatic alkaloids from marine invertebrates as cytotoxic compounds and inhibitors of multidrug resistance caused by P-glycoprotein", *Br. J. Cancer 74*: 677-682 (1996).
Heim, et al., "Biomimetic Synthesis of Lamellarin G Trimethyl Ether", *Ang. Chem. Int. Ed. Engl. 36*: 155-156 (1997).
Ishibashi, et al., "Total Syntheses of Lamellarin D and H. The First Synthesis of Lamellarin-Class Marine Alkaloids", *Tetrahedron 53*: 5951-5962 (1997).
Kang, et al., "Ningalins A-D: Novel Aromatic Alkaloids from a Western Australian Ascidian of the Genus *Didemnum*", *J. Org. Chem. 62*: 3254-3262 (1997).
Ebel, et al., "A Concise Synthesis of Storniamide A Nonamethyl Ether", *Tet. Lett. 39*: 9165-9166 (1998).
Boger, et al., "Total Syntheses of Ningalin A, Lamellarin O, Lukianol A, and Permethyl Storniamide A Utilizing Heterocyclic Azadiene Diels-Alder Reactions", *J. Am. Chem. Soc. 121*: 54-62 (1999).
Boger, et al., "Total Synthesis of Ningalin B Utilizing a Heterocyclic Azadiene Diels-Alder Reaction and Discovery of a New Class of Potent Multidrug Resistant (MDR) Reversal Agents", *J. Org. Chem. 65*: 2479-2483 (2000).

*Primary Examiner*—James O. Wilson
*Assistant Examiner*—Brenda Coleman
(74) *Attorney, Agent, or Firm*—Donald G. Lewis

(57) ABSTRACT

Anlogs of ningalin B lacking inherent cytotoxic activity may be employed to reverse multi-drug resistant (MDR) phenotype and to resensitize transformed cells, including a human colon cancer cell line (HCT116/VM46), with respect to a variety of cytotoxic agents, e.g., vinblastine and doxorubicin. In many instances, resensitization is achieved at lower doses than the prototypical agent verapamil. Total synthesis of ningalin B and its analogs was achieved using a concise, efficient approach based on a heterocyclic azadiene Diels-Alder strategy (1,2,4,5-tetrazine→1,2-diazine→pyrrole) ideally suited for construction of the densely functionalized pyrrole core found in the natural product is detailed.

20 Claims, 11 Drawing Sheets

Ningalin B (1)

| compound | L1210 | IC$_{50}$ (μM)$^a$ | | |
|---|---|---|---|---|
| | | HCT116 wild type | HCT116/VM46 (MDR) | HCT116/VP35 (reduced topo II) |
| ningalin B (1) | 10 | 12 | 60 | 30 |
| 7 | 10 | 40 | 60 | 60 |
| 8 | 50 | >100 | >100 | 100 |
| 10 | 80 | 90 | >100 | 70 |
| 11 | 6 | 6 | 40 | 10 |
| 12 | 30 | 70 | >100 | >100 |
| 13 | 50 | 30 | 40 | 30 |
| 14 | 90 | 60 | >100 | 70 |
| vinblastine | | 0.002 | 0.07 | |
| doxorubicin | | 0.01 | 0.07 | 0.06 |
| etoposide | | 0.5 | 40 | 40 |

$^a$Duplicate assays, average IC$_{50}$

Figure 6

| compound at 1.0 μM | vinblastine IC$_{50}$ (μM)$^a$ | gain in sensitivity$^b$ (% reversion) | doxorubicin IC$_{50}$ (μM)$^a$ | gain in sensitivity$^b$ (% reversion) |
|---|---|---|---|---|
| ningalin B (1) | 0.02 | 4 (10) | 0.5 | 0 |
| 7 | 0.02 | 4 (10) | 0.1 | 0 |
| 8 | 0.02 | 4 (10) | 0.1 | 0 |
| 10 | 0.004 | 18 (50) | 0.05 | 1 (20) |
| 10 (7.5 μM) | 0.002 | 35 (100) | 0.02 | 4 (50) |
| 11 | 0.002 | 35 (100) | 0.02 | 4 (50) |
| 11 (7.5 μM) | 0.0006 | 117 (330) | 0.009 | 8 (110) |
| 12 | 0.02 | 4 (10) | 0.07 | 1 (14) |
| 13 | 0.002 | 35 (100) | 0.02 | 4 (50) |
| 13 (7.5 μM) | 0.001 | 70 (200) | 0.01 | 7 (100) |
| 14 | 0.0007 | 100 (290) | 0.03 | 2 (33) |
| verapamil | | | | |
| (1.0 μM) | 0.02 | 10 (15) | 0.13 | |
| (7.5 μM) | 0.003 | 67 (100) | 0.05 | 1 (24) |

$^a$IC$_{50}$(μM) of vinblastine or doxorubicin against the MDR resistant cell line HCT116/VM46 in the presence of 1 μM (unless indicated otherwise) of the indicated compound. IC$_{50}$ values in the absence of added compound are 0.07 μM (vinblastine) and 0.01 μM (doxorubicin). For the wild-type HCT116 cell line not subject to MDR, IC$_{50}$ values are 0.002 μM (vinblastine) and 0.01 μM (doxorubicin).
$^b$Gain in sensitivity is measured as IC$_{50}$(-)/IC$_{50}$(+) [(-) = without added drug, (+) = with added drug]: Keller, R. P.; Altermatt, H. J.; Nooter, K.; Poschmann, G.; Laissue, J. A.; Bollinger, P.; Hiestand, P. C. *Int. J. Cancer* 1992, *50*, 593.

Figure 7

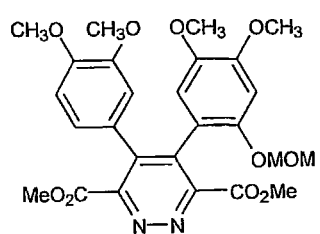
7
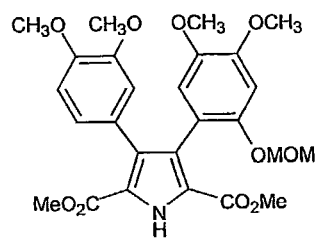
8
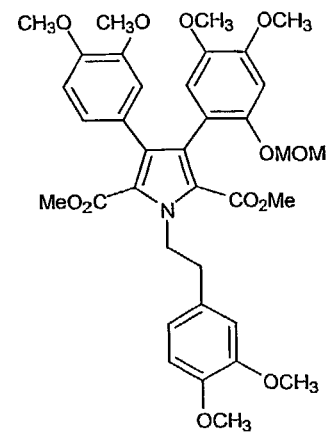
10
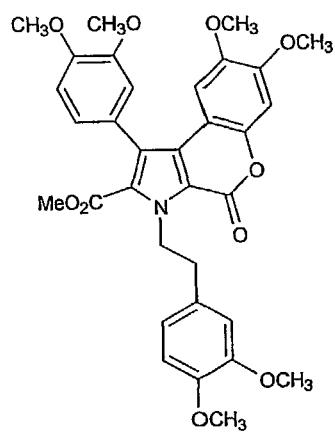
11
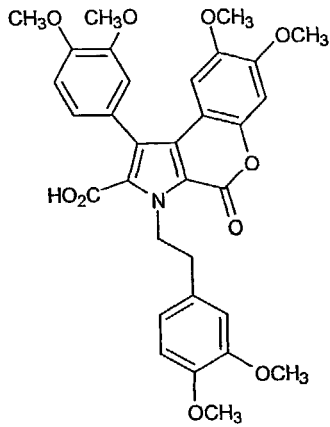
12
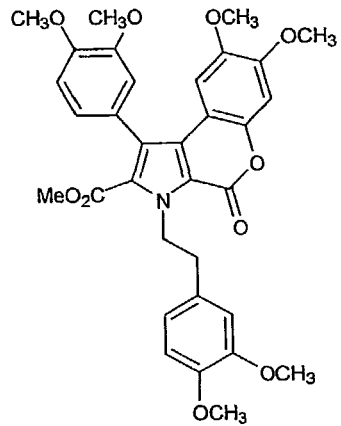
13
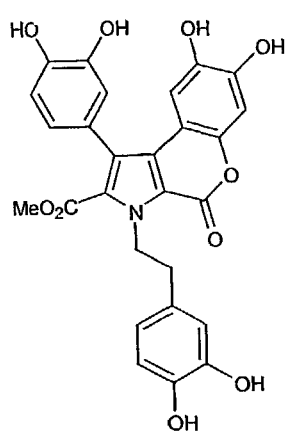
1
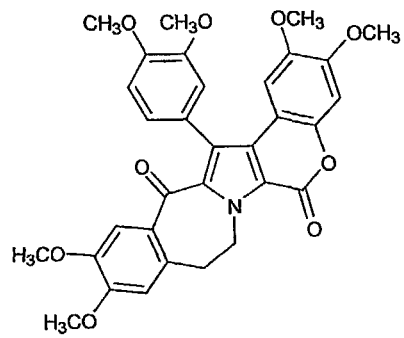
14
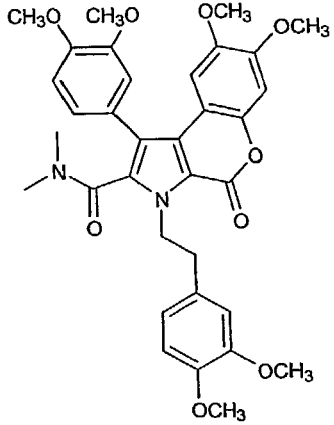
15
Figure 9

| compound | L1210 | HCT116 wild type | IC$_{50}$ (μM)[a] HCT116/VM46 (MDR) | HCT116/VP35 (reduced topo II) |
|---|---|---|---|---|
| 14 | 87 | 49 | 82 | 56 |
| 15 | 20 | 26 | 18 | 21 |

[a]Duplicate assays, average IC$_{50}$

Figure 10

| compound | vinblastine IC$_{50}$ (μM)$^a$ | gain in sensitivity$^b$ (% reversion) | doxorubicin IC$_{50}$ (μM)$^a$ | gain in sensitivity$^b$ (% reversion) |
|---|---|---|---|---|
| 14 (0.5 μM) | .0004 | 208 (250) | .04 | 168 (250) |
| 14 (0.1 μM) | .003 | 28 (33) | .1 | 67 (100) |
| 15 (7.5 μM) | .0001 | 830 (1000) | .009 | 744 (1110) |
| 15 (1.0 μM) | .001 | 83 (100) | .1 | 67 (100) |
| verapamil | | | | |
| (7.5 μM) | .0005 | 166 (200) | .06 | 112 (167) |
| (1.0 μM) | .004 | 21 (25) | .4 | 17 (25) |

$^a$IC$_{50}$ (μM) of vinblastine or doxorubicin against the MDR resistant cell line HCT116/VM46 in the presence of the indicated compound. IC$_{50}$ values in the absence of added compound are 0.08 μM (vinblastine) and 6.7 μM (doxorubicin). For the wild-type HCT116 cell line not subject to MDR, IC$_{50}$ values are 0.001 μM (vinblastine) and 0.1 μM (doxorubicin).

$^b$Gain in sensitivity is measured as IC$_{50}$(-) / IC$_{50}$(+) [(-) = without added drug, (+) = with added drug]: Keller, R. P.; Altermatt, H. J.; Nooter, K.; Poschmann, G.; Laissue, J. A.; Bollinger, P.; Hiestand, P. C. *Int. J. Cancer* 1992, *50*, 593.

Figure 11

NINGALIN B ANALOGS EMPLOYABLE FOR REVERSING MULTIDRUG RESISTANCE

CROSS-REFERENCE TO RELATED APPLICATIONS

This is a US national phase application of international application Serial No. PCT/US01/06811, filed Mar. 1, 2001 and published in English, which claims priority from and is a continuation-in-part application of U.S. provisional patent application Ser. No. 60/186,106, filed Mar. 1, 2000.

This invention was made with United States Government support under Contract No. CA 42056 from the National Institutes of Health. The United States Government has certain rights in the invention.

TECHNICAL FIELD

The invention relates to methods and reagents for reversing multidrug resistance (MDR) with respect to anticancer drugs. More particularly, invention relates to analogs of ningalin B and to their use as MDR reversal agents.

BACKGROUND

The recently identified ningalin class of marine natural products including ningalin B (1) possess a common 3,4-diaryl substituted pyrrole nucleus bearing a 2-carboxylate. Ningalin B (1) is the second member of this newly described family of marine natural products which were isolated by Fenical (1997) from an ascidian of the genus Didemnum collected in western Australia near Ningaloo Reef. (Kang, H.; Fenical, W. *J. Org. Chem.* 1997, 62, 3254) Consequently, 1 and the related ningalins are the newest members of a family of 3,4-dihydroxyphenylalanine (DOPA)-derived o-catechol metabolites that include the tunichromes. (Bruening, R. C.; et al. *J. Am. Chem. Soc.* 1985, 107, 5289; Bruening, R. C.; et al. *J. Nat. Prod.* 1986, 49, 193; Bayer, E; et al. *Angew. Chem. Int. Ed. Engl.* 1992, 31, 52; Oltz, E. M.; et al. *J. Am. Chem. Soc.* 1988, 110, 6162; Ryan, D. E.; et al. *J. Am. Chem. Soc.* 1992, 114, 9659; Taylor, S. W.; et al. *Arch. Biochem. Biophys.* 1995, 324, 228)

The lamellarins are a related rapidly growing class of marine natural products which were first isolated from the prosobranch mollusc Lamellaria sp. and important members of this class have been disclosed by Bowden, Faulkner, Fenical, Capon, and Scheuer. (Lamellarins A-D: Anderson, R. J.; et al. *J. Am. Chem. Soc.* 1985, 107, 5492. Lamellarins E-H: Lindquist, N.; et al. *J. Org. Chem.* 1988, 53, 4570. Lamellarins I-N: Carroll, A. R.; et al. *Aust. J. Chem.* 1993, 46, 489. Lamellarins O, P: Urban, S.; et al. *Aust. J. Chem.* 1994, 47, 1919. Lamellarins Q, R: Urban, S.; et al. *Aust. J. Chem.* 1995, 48, 1491. Lamellarins S: Urban, S.; et al. *Aust. J. Chem.* 1996, 49, 711. Lamellarins T-X: Reddy, R. M.; et al. *Tetrahedron* 1997, 53, 3457. Lamellarin Z: Davis, R. H.; et al. *J. Nat. Prod.* 1999, 62, 419. Lukianol A, B: Yoshida, W. Y.; et al. *Helv. Chim. Acta* 1992, 75, 1721.) Recent investigations of several lamellarins demonstrated their cytotoxic activity, revealed equally effective cytotoxic activity against multidrug-resistant (MDR) cell lines, and revealed MDR reversal even at noncytotoxic concentrations by inhibition of P-glycoprotein (P-gp) mediated drug efflux. (Quesada, A. R.; et al. *Br. J. Cancer* 1996, 74, 677.) Thus, they constitute a new class of antitumor agents which reverse MDR more effectively than verapamil and resensitize resistant malignant cells to front line therapeutics. A number of related structures have been defined that lack cytotoxic activity but which effectively reverse MDR. (Ningalin A, lamellarin O, lukianol A, and permethyl storniamide A: Boger, D. L.; et al. *J. Am. Chem. Soc.* 1999, 121, 54.)

What is needed is a new class of MDR reversal agents having potent activity for resensitizing resistant cancer cells with respect to effective anticancer agents.

SUMMARY

A concise total synthesis of ningalin B (1) is described enlisting a 1,2,4,5-tetrazine→1,2-diazine-pyrrole Diels-Alder strategy featuring the unusually effective [4+2] cycloaddition of the electron-deficient 1,2,4,5-tetrazine 2 with an unsymmetrical, electron-rich alkyne. Ningalin B is a member of a class of marine natural products characterized by a highly functionalized tetra- or pentasubstituted pyrrole which is ideally suited to construction using this strategy. While lacking inherent cytotoxic activity, the ningalin B synthetic precursors 10, 11, 13, 14, and 15, but not ningalin B itself, are shown to potently reverse MDR, resensitizing a resistant human colon cancer cell line (HCT116/VM46) to vinblastine and doxorubicin. These agents, including 14 bearing a novel ring system, constitute the members of a new class of effective MDR reversal agents.

More particularly, one aspect of the invention is directed to a compound represented by the following structure:

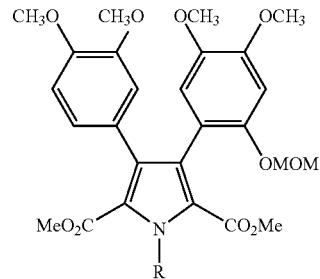

wherein R is a radical selected from the group consisting of H and the following structure:

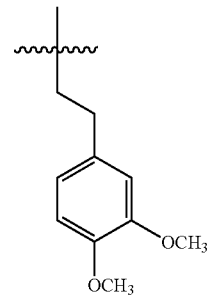

Preferred embodiments of this aspect of the invention include either of the following structures:

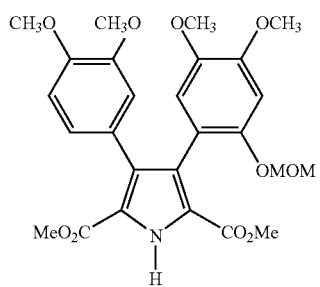
and
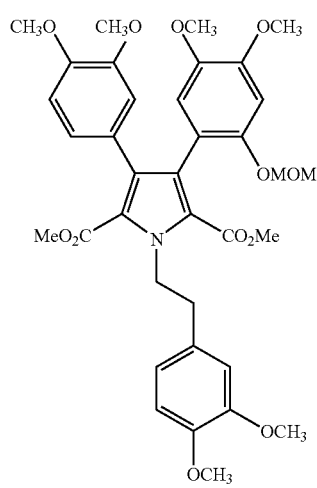
Another aspect of the invention is directed to a compound represented by the following structure:
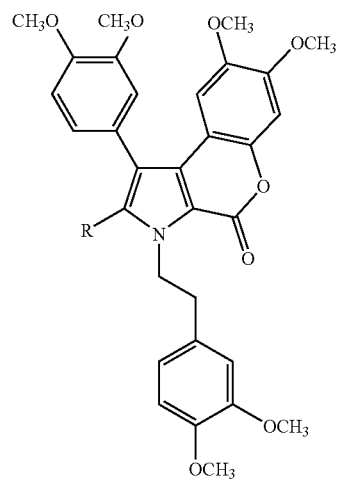
wherein R is a radical selected from the group consisting of H, $CO_2H$, $CO_2Me$ and $CON(Me)_2$. Preferred embodiments of this aspect of the invention include compounds represented by the following structures:
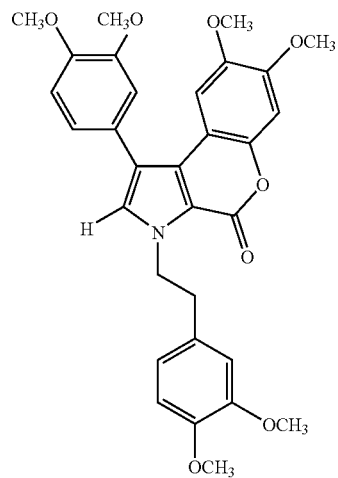
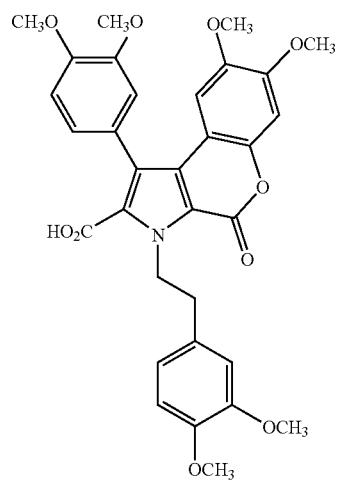
and
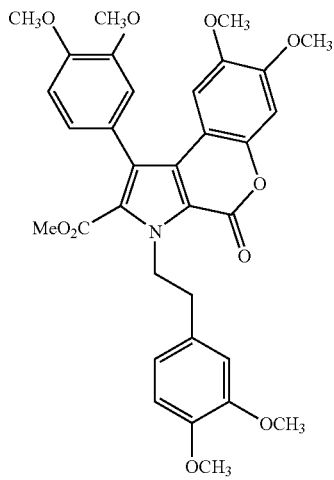

-continued

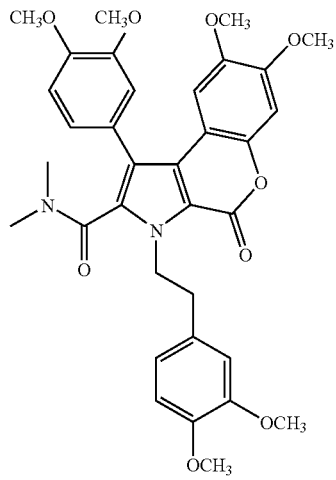

Another aspect of the invention is directed to an analog of ningalin B represented by the following structure:

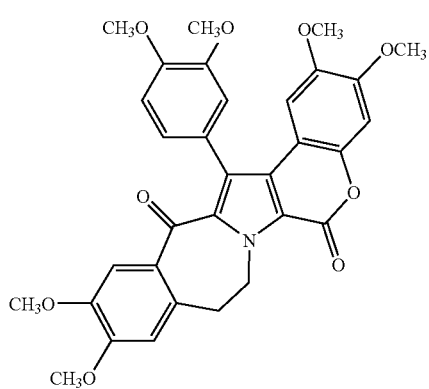

Another aspect of the invention is directed to a synthetic process comprising the step of cyclizing a precursor compound with an excess of Eaton's acid at room temperature under reaction conditions for producing an analog of ningalin B, the precursor compound, the analog of ningalin B, and the cyclization reaction being represented as follows:

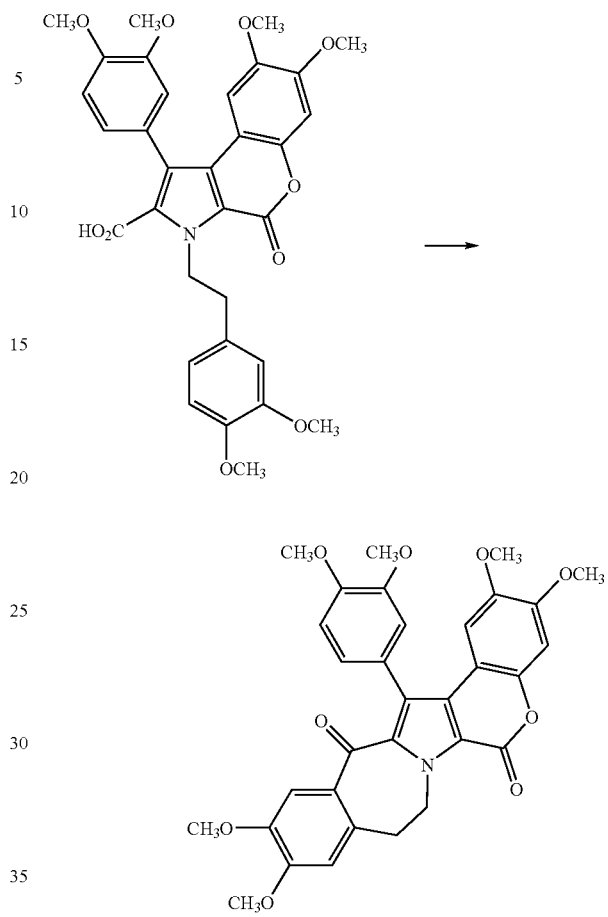

Another aspect of the invention is directed to a process for reversing multidrug resistance in a cancer cell. The process comprises the step of contacting the cancer cell with a concentration sufficient for reversing said multidrug resistance of a compound selected from a group consisting of any or all of the following structures:

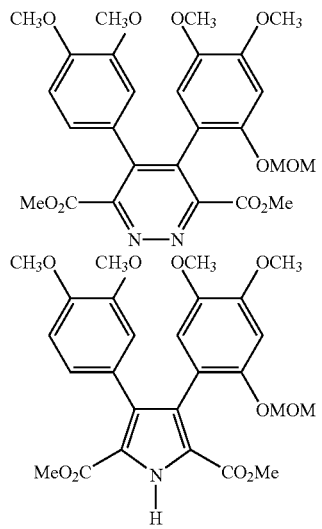

-continued
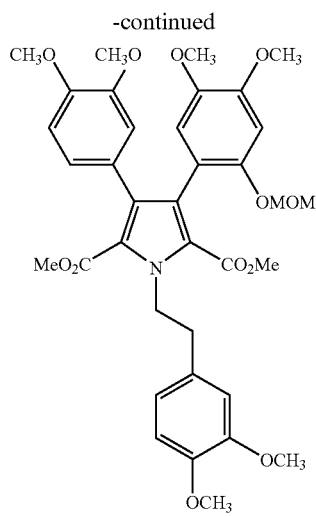
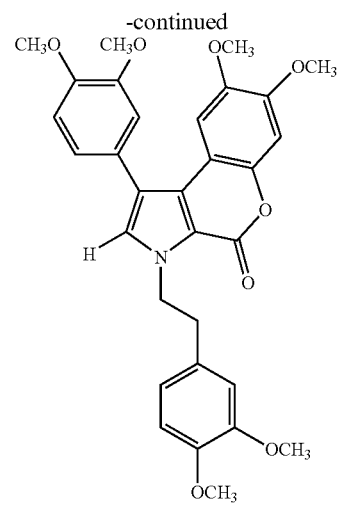
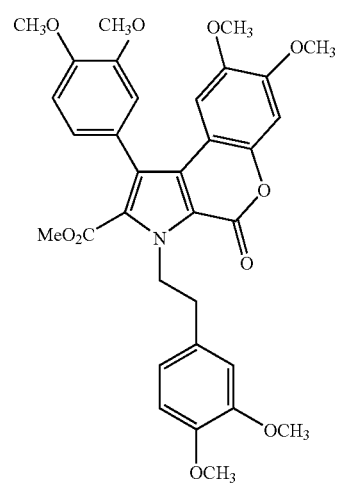
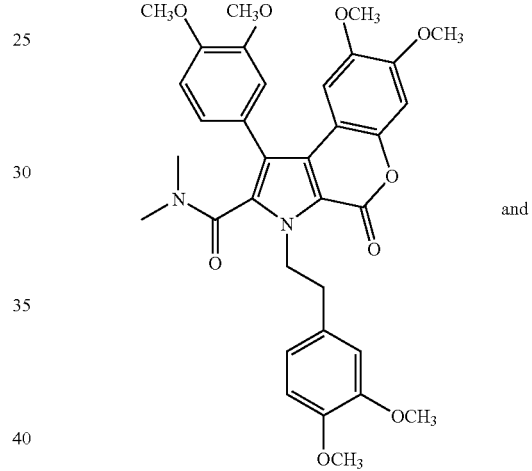
and
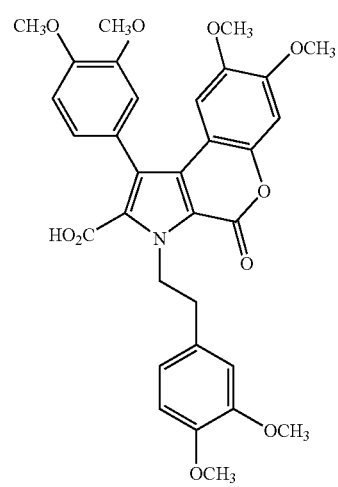
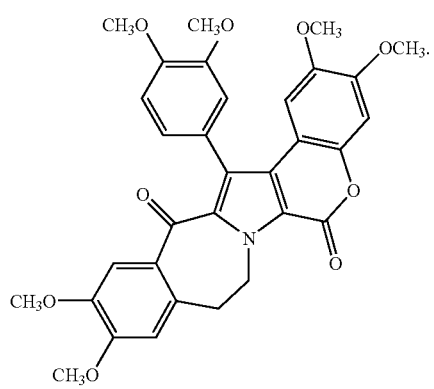
BRIEF DESCRIPTION OF FIGURES
FIG. 1 illustrates the structure of the natural product ningalin B.

FIG. 6 illustrates a table with a comparison of the cytotoxic activity of ningalin B and some analogs with some commonly used compounds against three different cell lines.

FIG. 7 illustrates a table with a comparison of the ability of ningalin B and its analogs to reverse multidrug resistance in the HCT116/VM46 cell line.

Figure 8:
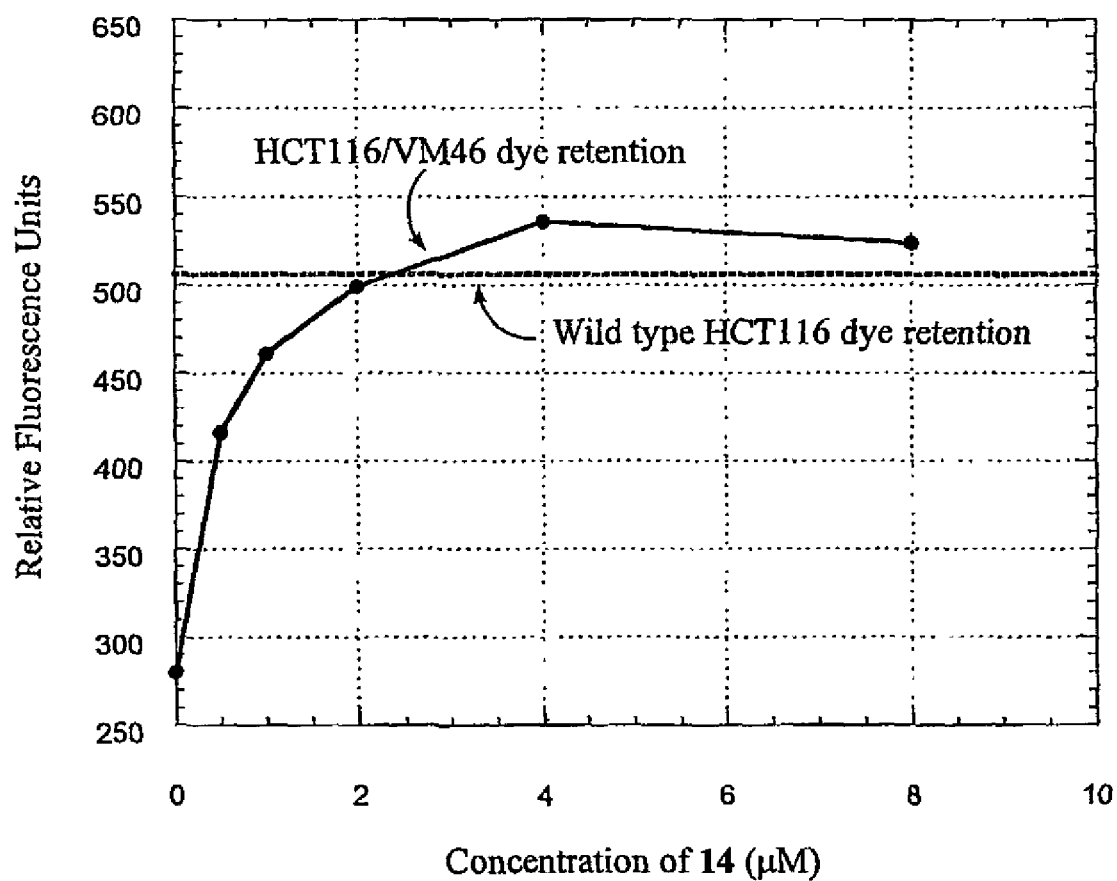

FIG. 8 illustrates the inhibition of dye efflux (rhodamine 123) from the HCT116/VM46 cell line. Accumulation of rhodamine 123 in the HCT116/VM46 cell line after 30 min incubation in 40 mM rhodamine in phosphate buffer solution (Quesada, A. R.; et al., Br. J. Cancer 1996, 74, 677).

FIG. 9 illustrates the structures of the analogs and ningalin B.

FIG. 10 illustrates data on the cytotoxicity of compounds 14 and 15 against four cancer cell lines, according to the method of FIG. 6.

FIG. 11 illustreates further data on the reversal of multidrug resistance (MDR) by compounds 14 and 15 with respect to vinblastine and doxorubicin against the cell line HCT116/VM46.

DETAILED DESCRIPTION

Figure 1:
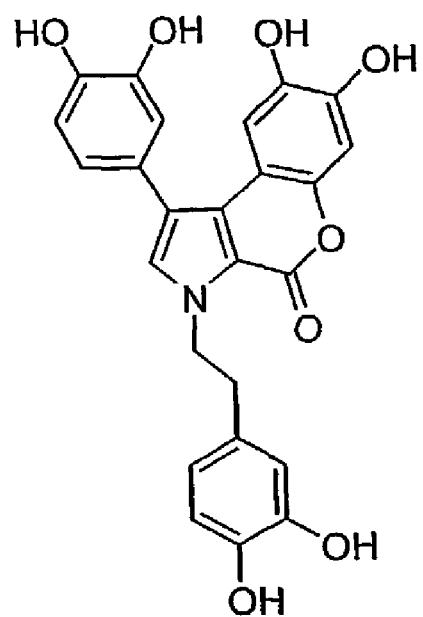
Figure 2:
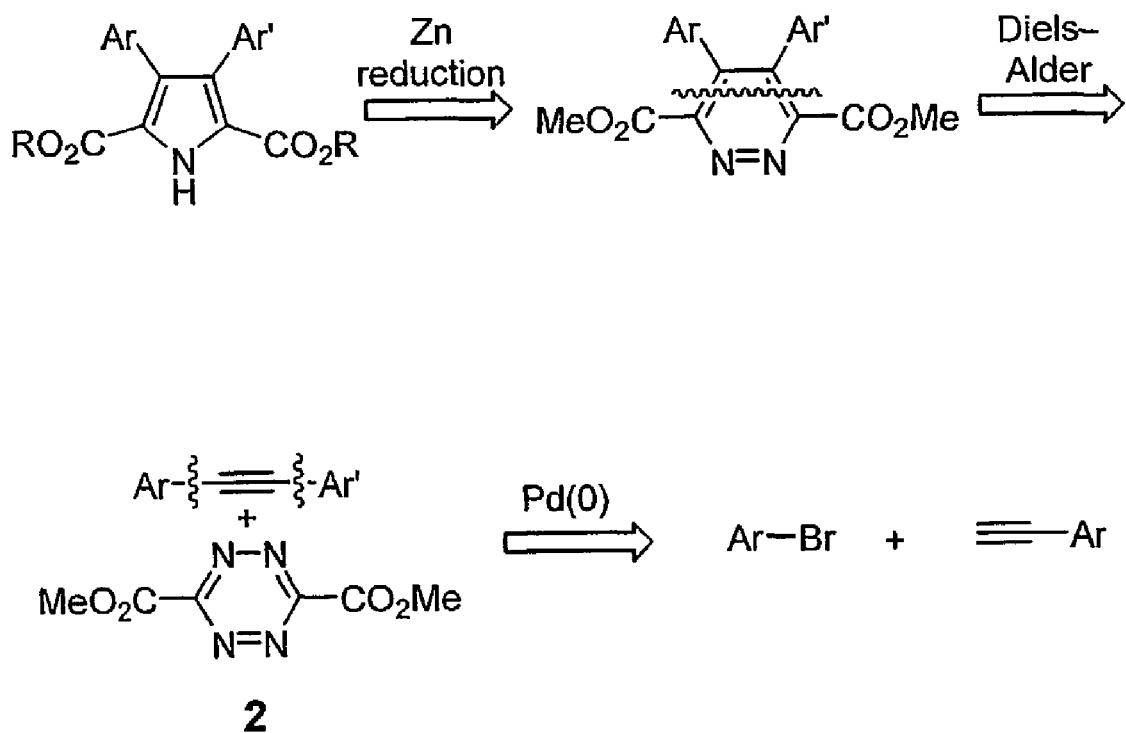
FIG. 2 illustrates a retrosynthetic scheme for synthesizing ningalin B and its analogs.

The total synthesis of ningalin B (1) and a number of structurally related synthetic analogs is described herein. Also described herein is a biological evaluation of the natural product and its synthetic analogs. The synthetic approach, complementary to the efforts described to date, (Lukianol A and lamellarin O dimethyl ether: Fürster, A.; et al. J. Org. Chem. 1995, 60, 6637. Lamellarin O and Q, lukianol A: Banwell, M. G.; et al. Chem. Commun. 1997, 207. Lamellarin K: Banwell, M.; et al. Chem. Commun. 1997, 2259. Lamellarin D and H: Ishibashi, F.; et al. Tetrahedron 1997, 53, 5951. Lamellarin G trimethyl ether: Heim, A.; et al. Angew. Chem. Int. Ed. Engl. 1997, 36, 155. Storniade A nonamethyl ether: Ebel, H.; et al. Tetrahedron Lett. 1998, 39, 9165. Polycitrin A: Terpin, A.; et al. Tetrahedron 1995, 51, 9941.) employs a heteroaromatic azadiene Diels-Alder reaction (Boger, D. L. Chemtracts: Org. Chem. 1996, 9, 149. Boger, D. L. Bull. Clim. Soc., Belg. 1990, 99, 599. Boger, D. L.; et al. In Progress in Heterocyclic Chem. 1989; Suschitzky, H.; Scriven, E. F. V., Eds.; Pergamon: Oxford, Vol. 1; 1989, 30. Boger, D. L.; et al. Hetero Diels-Alder Methodology in Organic Synthesis; Academic: San Diego, 1987. Boger, D. L.; et al. Chem. Rev. 1986, 86, 781. Boger, D. L. Tetrahedron 1983, 39, 2869.) to assemble the substituents onto a six-membered 1,2-diazine core which is followed by a reductive ring contraction reaction (Boger, D. L.; et al. J. Org. Chem. 1984, 49, 4405. Boger, D. L.; et al. J. Org. Chem. 1988, 53, 1405. Boger, D. L.; et al. J. Am. Chem. Soc. 1993, 115, 11418. Boger, D. L.; et al. J. Org. Chem. 1985, 50, 5377. Boger, D. L.; Org. Syn. 1991, 70, 79.) to provide the corresponding pyrrole (FIG. 2).

Figure 3:
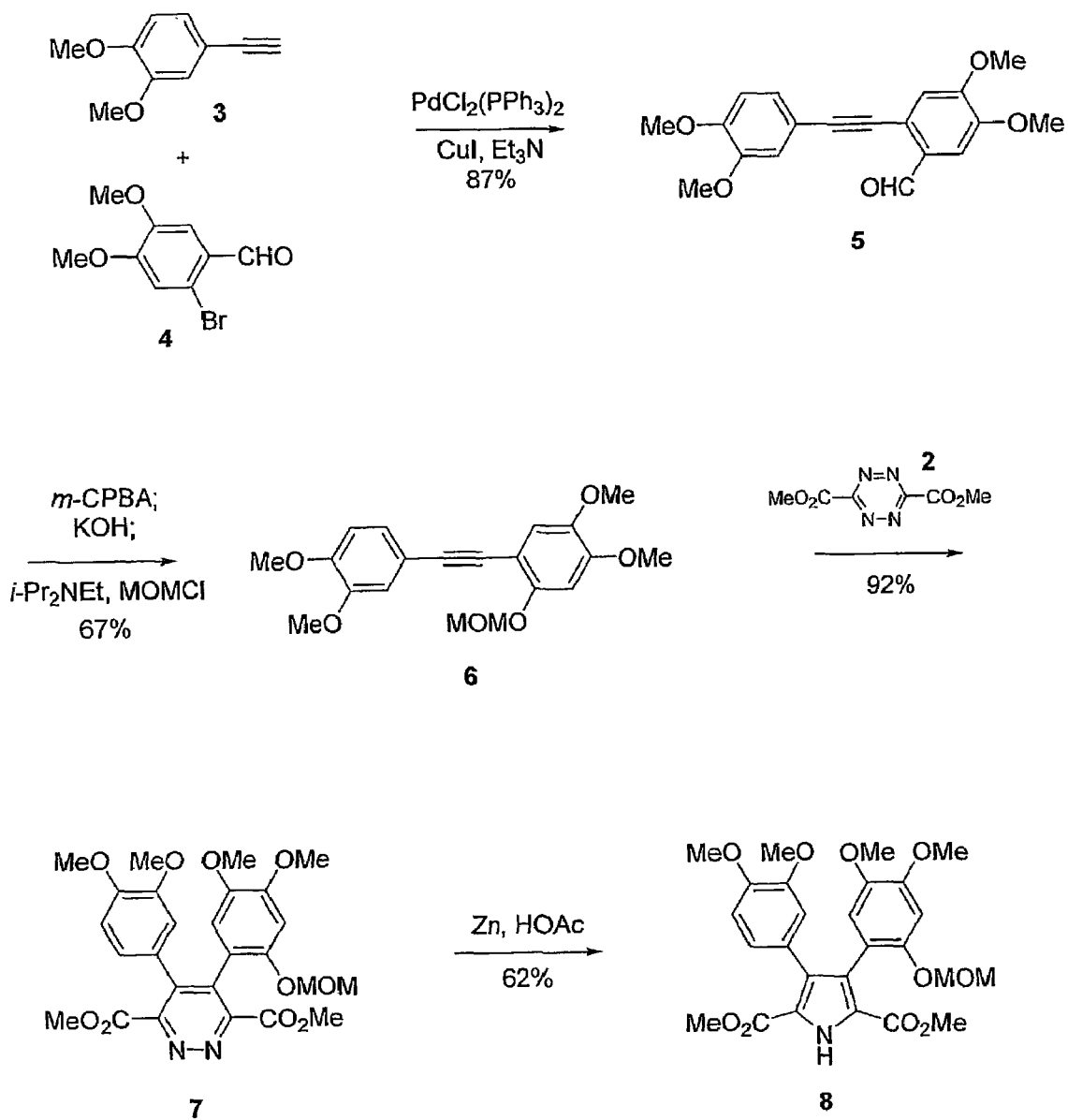
FIG. 3 illustrates the first portion of the synthetic scheme used to synthesize ningalin B.
Figure 4:
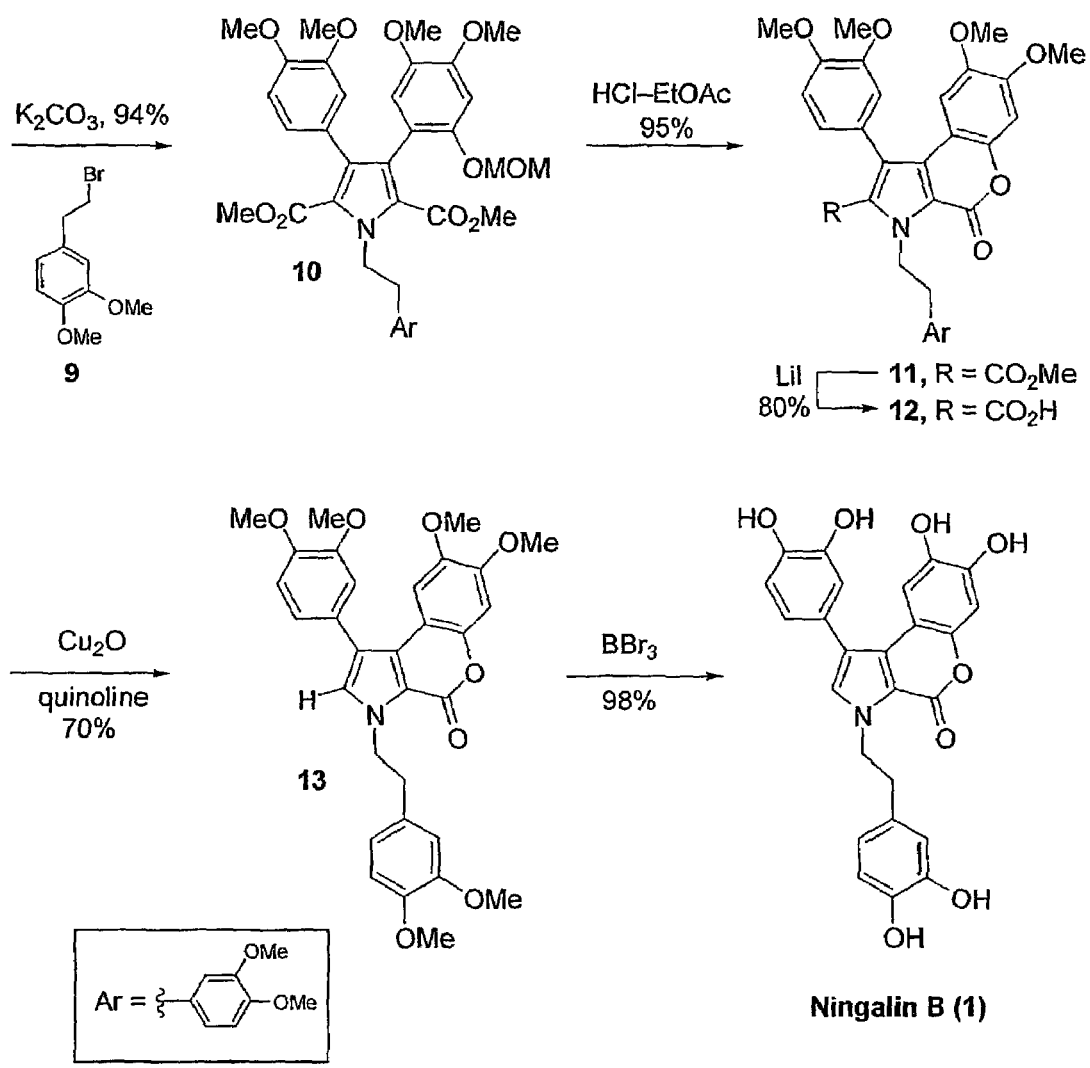
FIG. 4 is a continuation of FIG. 3 and illustrates the completion of the synthesis of ningalin B.

Total Synthesis of Ningalin B. The requisite diphenylacetylene 5 was prepared by a palladium(0)-catalyzed cross-coupling of the terminal acetylene 3 (Upasami, R. B.; et al. J. Med. Chem. 1997, 40, 73.) and 4 (0.05 equiv Pd(0), 0.3 equiv CuI, $Et_3N$, 87%) in which slow addition of the acetylene was necessary to suppress competitive formation of the coupled diacetylene (FIG. 3). Conversion to the methoxymethyl ether 6 was accomplished by Baeyer-Villiger oxidation of aldehyde 5 (1.2 equiv m-CPBA), formate hydrolysis (KOH), and subsequent protection of the phenol (3.0 equiv MOMCl, 4.0 equiv $i-Pr_2NEt$, 67% overall). The first of the two key conversions, the Diels-Alder reaction of the electron-rich acetylene 6 with the electron-deficient 1,2,4,5-tetrazine 2, (Boger, D. L.; et al. J. Org. Chem. 1985, 50, 5377. Boger, D. L.; et al. Org. Synth. 1991, 70, 79.) proceeded to give the desired 1,2-diazine 7 in excellent yield (mesitylene, 140° C., 92%). The relative facility of this inverse electron demand [4+2] cycloaddition may be attributed to the electron-donating properties of the dienophile aryl alkoxy groups. Thus, the oxygenation pattern found in the diaryl acetylene 6 increases the nucleophilic character and improves what is a typically poor reactivity of an alkyne towards 2. (Sauer, J.; et al. Chem. Ber. 1965, 98, 1435) Subsequent reductive ring contraction (Zn, HOAc, 62%) of 7 afforded the core pyrrole structure found in the natural product. N-Alkylation with the phenethyl bromide 9 (Lan, A. J. Y.; et al. J. Am. Chem. Soc. 1987, 109, 2738) (5.0 equiv, $K_2CO_3$, 94%) and subsequent MOM deprotection with concomitant lactonization (HCl-EtOAc, 95%) provided mono-lactone 11. (FIG. 4) Selective hydrolysis of the methyl ester (LiI, 80%) and decarboxylation ($Cu_2O$, quinoline, 220° C., 5 min, 70%) afforded hexamethyl ningalin B (13). Decarboxylation with alternative copper sources or those conducted at lower temperatures or with longer reaction times resulted in lower yields (0-44%). Exhaustive demethylation with $BBr_3$ completed the total synthesis of ningalin B and provided material identical in all respects ($^1$H NMR, $^{13}$C NMR, IR, MS) with authentic material. (Kang, H.; Fenical, W. J. Org. Chem. 1997, 62, 3254.)

Figure 5:
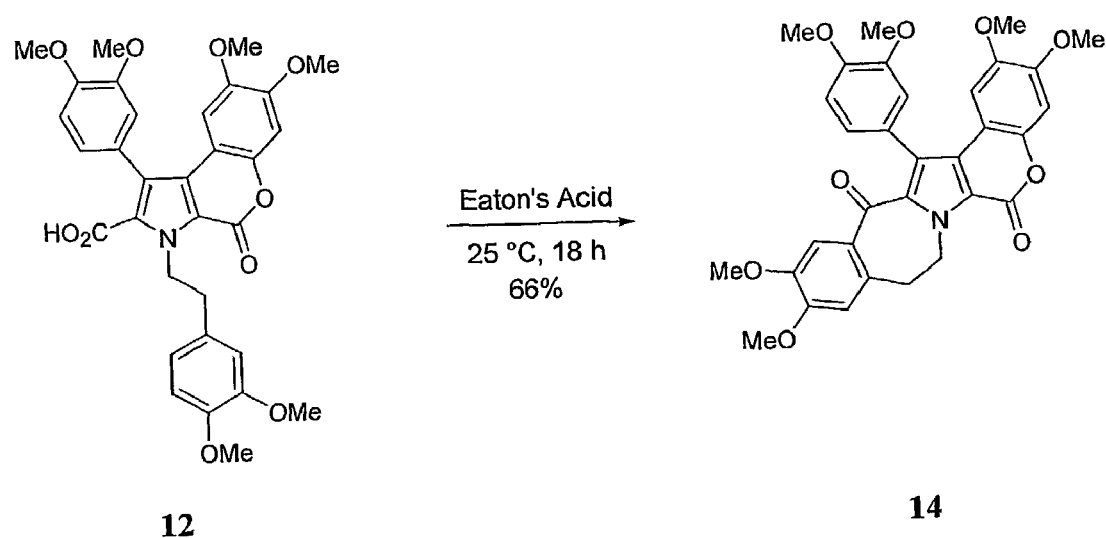
FIG. 5 illustrates the product obtained from an attempted decarboxylation of structure 12 using Eaton's acid.

Initial attempts to promote decarboxylation under acidic conditions resulted in either no reaction (neat TFA, 60° C., 12 h) or Friedel-Crafts acylation (neat Eaton's acid, 25° C., 18 h) to provide 14 (FIG. 5). Although not the object of the present efforts, the fused tricyclic ring system consisting of a 7-membered ketone flanked by an aryl group and a pyrrole has been formed by Friedel-Crafts acylation in the synthesis of cephalotaxus alkaloids. (Girard, Y.; et al. J. Org. Chem. 1983, 48, 3220. Weinstein, B.; et al. J. Org. Chem. 1976, 41, 875.) Based on the precedented ease of formation of the 7-membered ring and $^1$H and HMBC NMR spectroscopy, formation of the alternative 5-membered ring was excluded. Importantly, 14 proved to be the most potent MDR reversal agent identified in this series, causing hypersensitivity towards vinblastine in the HCT/VM46 MDR-cell line.

Cytotoxic Activity and Reversal of Multidrug Resistance. A number of compounds in the structurally related lamellarin class of natural products possess cytotoxic activity. (Quesada, A. R.; et al. Br. J. Cancer 1996, 74, 677.) With exception of ningalin A, (Ningalin A, lamellarin O, lukianol A, and permethyl storniamide A: Boger, D. L.; et al. J. Am. Chem. Soc. 1999, 121, 54.) the biological evaluation of the ningalin family has not been explored. Consequently, ningalin B and a number of structurally related synthetic intermediates were tested in a L1210 cytotoxic assay, and the results are summarized in FIGS. 6 and 10. Ningalin B was found to be only moderately active against both the L1210 and HCT116 cell lines, and a number of synthetic intermediates displayed a similar level of activity due to their comparable structures. Notably, the O-methyl derivative of ningalin B is 5-fold less active against L1210 and 2.5-fold less active against HCT116 than ningalin B, in agreement with previous studies where an increase in the extent of O-methylation results in a decrease in cytotoxic activity. (Ningalin A, lamellarin O, lukianol A, and permethyl storniamide A: Boger, D. L.; et al. *J. Am. Chem. Soc.* 1999, 121, 54.)

More importantly, a select set of the naturally occurring lamellarins have been shown to exhibit equally potent cytotoxic activity against multidrug resistant (MDR) cell lines due to overexpression of P-glycoprotein and to reverse MDR at noncytotoxic concentrations, resensitizing the resistant cell lines to conventional therapeutic agents. (Quesada, A. R.; et al. *Br. J. Cancer* 1996, 74, 677.) P-gp is a 170 kDa plasma membrane glycoprotein encoded in humans by the MDR1 gene which exports drugs out of mammalian cells, lowering their intracellular concentration. (Patel, N. H.; et al. *Invest. New Drugs* 1994, 12, 1. Gottesman, M. M.; et al. *Annu. Rev. Biochem.* 1993, 62, 385.) Therefore, 7-14 were also tested against a wild-type human colon cancer cell line (HCT116) and two resistant HCT116 cell lines. The first resistant cell line (HCT116/VM46) embodies the MDR phenotype and overexpresses P-glycoprotein while the second cell line (HCT116/VP35) derives its resistance through underexpression of topoisomerase II. The examination of the latter cell line along with the wild-type HCT116 and their comparison with HCT116VM46 allows an accurate assessment of the MDR sensitivity as well as an assessment of one potential therapeutic target. All of the agents examined showed little or no intrinsic cytotoxic activity against either HCT116 or the resistant cell lines.

Fundamentally more important, many of the agents were found capable of reversing MDR at noncytotoxic concentrations, resensitizing HCT116/VM46 to vinblastine and doxorubicin (FIGS. 7 and 11). As illustrated in FIGS. 7 and 11, solutions of physiological buffer suitable for injection or infusion were prepared and admixed with ningalin B and its analogs for testing as MDR reversal agents. Of the compounds examined, 10, 11, 13, and 14 were able to resensitize HCT116/VM46 to vinblastine and doxorubicin at 1 µM and to do so more effectively than verapamil. While lacking inherent cytotoxicity, 11 and 13 showed complete MDR reversal at this concentration and 14 caused hypersensitivity of HCT116/VM46 to vinblastine, exhibiting an $IC_{50}$ value 3× lower than wild type treatment with vinblastine alone. At the higher concentrations required for complete reversal by verapamil (7.5 µM), 10 showed complete MDR reversal and the HCT116/VM46 cell line became hypersensitive to vinblastine in the presence of 11 and 13. The HCT116/VP35 resistant cell line showed no resensitization towards vinblastine or doxorubicin in the presence of the examined agents, indicating that the MDR reversal activity is due to interaction with P-gp. Consistent with its action on Pgp-170, 14 inhibited dye efflux (Quesada, A. R.; et al. *Br. J. Cancer* 1996, 74, 677.) (rhodamine 123) from HT116/VM46, returning the dye retention to levels equivalent to that of wild type HCT116 (FIG. 8).

EXAMPLES

2-[(3,4-Dimethoxyphenyl)ethynyl]-4,5-dimethoxybenzaldehyde (5). A stirred solution of 4 (2.7 g, 11 mmol, 1.0 equiv), $PdCl_2(PPh_3)_2$ (0.39 g, 0.55 mmol, 0.05 equiv) and CuI (0.63 g, 3.31 mmol, 0.3 equiv) in 5:1 DMF-$Et_3N$ (106 mL) under Ar at 75° C. was treated with 3[12] (2.23 g, 13.8 mmol, 1.25 equiv) in 5:1 DMF-$Et_3N$ (42 mL) over a period of 2.5 h. The reaction mixture was allowed to stir for an additional 1.5 h before it was cooled to 25° C. and concentrated under reduced pressure. Chromatography ($SiO_2$, 4.5 (20 cm, $CH_2Cl_2$) afforded 5 (1.50 g, 87% yield) as a yellow solid: mp 148-149° C. (EtOAc-hexanes); FABHRMS (NBA/NaI) m/z 327.1228 (M+H$^+$, $C_{19}H_{18}O_5$ requires 327.1232).

2-[(3,4-Dimethoxyphenyl)ethynyl]-4,5-dimethoxy-1-(methoxymethoxy)-benzene (6). A stirred solution of 5 (3.13 g, 9.60 mmol, 1.0 equiv) in $CH_2Cl_2$ (380 mL under Ar at 25° C. was treated with $Na_2HPO_4$ (3.27 g, 23.03 mmol, 2.4 equiv) and m-CPBA (3.98 g, 11.52 mmol, 1.2 equiv). After 18 h, the mixture was diluted with saturated aqueous $NaHCO_3$, extracted with EtOAc, washed with saturated aqueous $NaHCO_3$ and saturated aqueous NaCl, dried ($Na_2SO_4$), and concentrated under reduced pressure. The formate was redissolved in MeOH (120 mL), treated with 10% aqueous KOH (7.8 mL, 15.6 mmol, 1.6 equiv), and the mixture was stirred at 25° C. for 1.5 h. The reaction was quenched with the addition of 10% aqueous HCl, extracted with $CH_2Cl_2$, washed with $H_2O$, dried ($Na_2SO_4$), and the solvent was removed under reduced pressure. An analytically pure sample of the phenol could be prepared by chromatography ($SiO_2$, 5% EtOAc/$CH_2Cl_2$): mp 164-165° C. (EtOAc-hexanes); MALDIHRMS (DHB) m/z 337.1058 (M+Na$^+$, $C_{18}H_{18}O_5$ requires 337.1046). A solution of the crude phenol in $CH_2Cl_2$ (100 mL) under Ar at 0° C. was treated with $^iPr_2NEt$ (6.70 mL, 38.4 mmol, 4.0 equiv) and chloromethyl methyl ether (2.19 mL, 28.8 mmol, 3.0 equiv). The mixture was warmed to 25° C. and allowed to stir for 18 h. Following dilution with $H_2O$, the mixture was extracted with $CH_2Cl_2$, washed with saturated aqueous $NaHCO_3$, saturated aqueous NaCl, dried ($Na_2SO_4$), and concentrated under reduced pressure. Chromatography ($SiO_2$, 4.5 (15 cm, 5% EtOAc/$CH_2Cl_2$) afforded 6 (2.32 g, 67% yield) as an orange solid: mp 84-86° C. (EtOAc-hexanes); MALDIHRMS (DHB) m/z 358.1411 (M$^+$, $C_{20}H_{22}O_6$ requires 358.1416).

Dimethyl 4-(4,5-Dimethoxy-2-(methoxymethoxy)phenyl)-5-(3,4-dimethoxyphenyl)-1,2-diazine-3,6-dicarboxylate (7). A solution of 6 (1.10 g, 3.07 mmol, 1.0 equiv) and 3,6-dicarbomethoxy-1,2,4,5-tetrazine (2,[13] 0.91 g, 4.60 mmol, 1.5 equiv) in mesitylene (15.4 mL) was warmed at 140° C. under Ar for 24 h. Additional 2 (0.91 g, 4.60 mmol, 1.5 equiv) was added, and the mixture was maintained at 140° C. for an additional 24 h before the reaction mixture was cooled to 25° C. and the solvent was evaporated. Chromatography ($SiO_2$, 4.5 (20 cm, 30% EtOAc/$CH_2Cl_2$) provided 7 (1.49 g, 92% yield) as an orange oil. An analytically pure sample was prepared by recrystallization from EtOAc-hexanes: mp 131-133° C.; FABHRMS (NBA/NaI) m/z 551.1663 (M+Na$^+$, $C_{26}H_{28}N_2O_{10}$ requires 551.1642).

Dimethyl 3-(4,5-Dimethoxy-2-(methoxymethoxy)phenyl)-4-(3,4-dimethoxyphenyl)pyrrole-2,5-dicarboxylate (8). A solution of 7 (1.01 g, 1.91 mmol, 1.0 equiv) in HOAc (25 mL) under Ar at 25° C. was treated with activated Zn dust (1.25 g, 19.1 mmol, 10 equiv), stirred for 4 h, and then treated with additional Zn dust (1.25 g, 10 equiv). After 14.5 h, the slurry was diluted with 10% MeOH/$CHCl_3$ (25 mL) and stirred 3 h at 25° C. The mixture was filtered through Celite, rinsed with 10% MeOH/$CHCl_3$, and the filtrate was washed with saturated aqueous $NaHCO_3$, dried ($Na_2SO_4$), and concentrated in vacuo. Chromatography ($SiO_2$, 4.5×15 cm, 25% EtOAc/$CH_2Cl_2$) afforded 8 (0.61 g, 62% yield) as an orange oil. An analytically pure sample could be prepared by recrystallization from EtOAc-hexanes: mp 162-163° C.; MALDIHRMS (DHB) m/z 515.1800 (M$^+$, $C_{26}H_{29}NO_{10}$ requires 515.1791).

Dimethyl 3-(4,5-Dimethoxy-2-(methoxymethoxy)phenyl)-4-(3,4-dimethoxyphenyl)-1-[2-(3,4-dimethoxyphenyl)

ethyl]pyrrole-2,5-dicarboxylate (10). A stirred mixture of 8 (297 mg, 0.58 mmol, 1.0 equiv), 3,4-dimethoxyphenethyl bromide (9,[15] 707 mg, 2.88 mmol, 5.0 equiv), and $K_2CO_3$ (398 mg, 2.88 mmol, 5 equiv) in DMF (5.8 mL) under Ar was warmed to 70° C. After 2.5 h, the mixture was cooled to 25° C. and solvent was removed in vacuo. Chromatography ($SiO_2$, 3.5×15 cm, 20% $EtOAc/CH_2Cl_2$) provided 10 (372 mg, 94% yield) as a yellow oil: FABHRMS (NBA/NaI) m/z 702.2553 ($M+Na^+$, $C_{36}H_{41}NO_{12}$ requires 702.2526).

Methyl 7,8-Dimethoxy-3-(2-(3,4-dimethoxyphenyl) ethyl)-1-(3,4-dimethoxyphenyl)-[1]-benzopyrano[3,4-b] pyrrol-4(3B)-one-2-carboxylate (11). A sample of 10 (272 mg, 400 µmol, 1.0 equiv) was treated with 3 M HCl-EtOAc (16 mL) and stirred under Ar at 25° C. for 2 h. Chromatography of the concentrated mixture ($SiO_2$, 4.5×5 cm, 15% $EtOAc/CH_2Cl_2$) afforded pure 11 (229 mg, 95%) as a light yellow solid: mp 192-193° C.; FABHRMS (NBA/NaI) m/z 626.2017 ($M+Na^+$, $C_{33}H_{33}NO_{10}$ requires 626.2002).

7,8-Dimethoxy-3-(2-(3,4-dimethoxyphenyl)ethyl)-1-(3,4-dimethoxyphenyl)-[1]-benzopyrano[3,4-b]pyrrol-4(3B)-one-2-carboxylic Acid (12). A stirred mixture of 11 (120 mg, 0.20 mmol, 1.0 equiv) and LiI (80 mg, 0.60 mmol, 3.0 equiv) in DMF (13 mL) under Ar was warmed at reflux. After 24 and 48 h, the reaction was treated with additional LiI (80 mg, 2×3 equiv). The mixture was warmed for a total of 3.5 d before the reaction was diluted with $H_2O$, acidified with 10% aqueous HCl, extracted with $CH_2Cl_2$, and dried ($Na_2SO_4$). Chromatography ($SiO_2$, 2.0×15 cm, 5% $MeOH/CHCl_3$) afforded 12 (94 mg, 80% yield) as a yellow solid: mp 219-220° C.; MALDIHRMS (DHB) mn/z 589.1940 ($M^+$, $C_{32}H_{31}NO_{10}$ requires 589.1948).

Hexamethyl Ningalin B (13). A solution of 12 (9.3 mg, 16 µmol, 1.0 equiv) and cuprous oxide[18] (2.3 mg, 16 µmol, 1.0 equiv) in degassed quinoline (450 µL) was warmed at 220° C. under Ar for 5 min. The mixture was cooled to 25° C., and the solvent was removed by a stream of $N_2$. Chromatography ($SiO_2$, 0.5×10 cm, 10% $EtOAc/CH_2Cl_2$) provided 13 (6.0 mg, 70% yield) as a white solid: mp 186-187° C.; MALDIHRMS (DHB) mn/z 546.2111 ($M+H^+$, $C_{31}H_{31}NO_8$ requires 546.2128).

Ningalin B (1). A solution of 13 (5.9 mg, 11 µmol, 1.0 equiv) in $CH_2Cl_2$ (1.1 mL) under Ar at −78° C. was treated with $BBr_3$ (1 M in hexanes, 160 µL, 160 µmol, 15 equiv), and the mixture was allowed to warm to 25° C. over 24 h. Following dilution with MeOH (0.50 mL), the solvent was removed by a stream of $N_2$ to afford synthetic 1 (5.2 mg, 98%) identical in all respects ($^1$H NMR, $^{13}$C NMR, IR, MS) when compared to spectra of naturally derived ningalin B: MALDIHRMS (DHB) m/z 484.1009 ($M+Na^+$, $C_{25}H_{19}NO_8$ requires 484.1008).

9,10-Dihydro-12,13-dimethoxy-1-(3',4'-dimethoxyphenyl)-3,4-dimethoxy-[4,3-d]-[1]-benzopyrano-15H-benzazepino[3,2-a]-[3]-pyrrol-7,15(18H)-dione (14). A sample of 12 (3.3 mg, 5.6 µmol, .1.0 equiv) was treated with Eaton's Acid[19] (200 µL, 7.5% $P_2O_5$—$MeSO_3H$) and stirred under Ar at 25° C. After 18 h, the reaction was diluted with $H_2O$, extracted with $CH_2Cl_2$, washed with saturated aqueous $NaHCO_3$ and saturated aqueous NaCl, dried ($Na_2SO_4$), and concentrated under reduced pressure. Chromatography ($SiO_2$, 1.5×5 cm, 10% $EtOAc/CH_2Cl_2$) afforded 14 (2.1 mg, 66% yield) as a yellow solid: mp 225-226° C.; MALDIHRMS (DHB) m/z 572.1940 ($M+H^+$, $C_{32}H_{29}NO_9$ requires 572.1921).

N,N-Dimethyl 7,8-Dimethoxy-3-(2-(3,4-dimethoxyphenyl)ethyl)-1-(3,4-dimethoxyphenyl)-[1]-benzopyrano[3,4-b]pyrrol-4(3H)-one-2-carboxamide (15). A solution of 12 (58.1 mg, 0.098 mmol, 1.0 equiv), EDCI (37.5 mg, 0.196 mmol, 2.0 equiv), and HOBt (26.5 mg, 0.196 mmol, 2.0 equiv) in $CH_2Cl_2$ (4 mL) under Ar at 25° C. was treated with $(CH_3)_2NH$ (2M in THF, 735 µL, 1.47 mmol, 15 equiv). After 16 h, the solvent was removed and chromatography ($SiO_2$, 1.5×12 cm, 1% $MeOH/CHCl_3$) afforded pure 15 (58.5 mg, 97% yield) as a white glass: MALDIHRMS (DHB) m/z 617.2500 ($M+H^+$, $C_{34}H_{36}N_2O_9$ requires 617.2494).

What is claimed is:

1. A compound represented by the following structure:

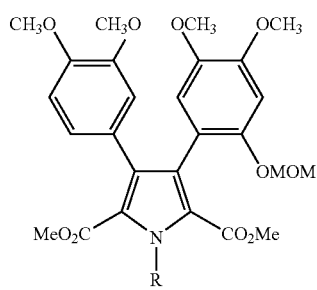

wherein R is a radical selected from the group consisting of H and the following structure:

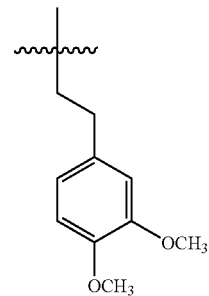

2. A compound according to claim 1 represented by the following structure:

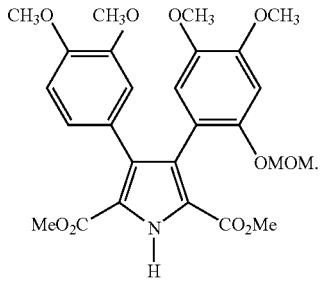

3. A compound according to claim 1 represented by the following structure:

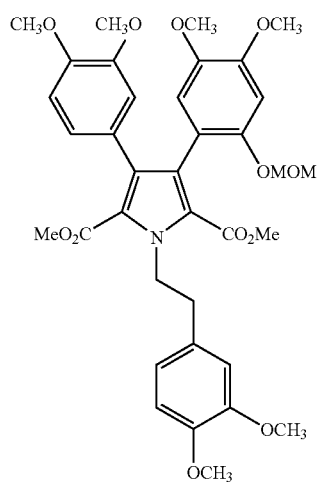
4. A compound represented by the following structure:
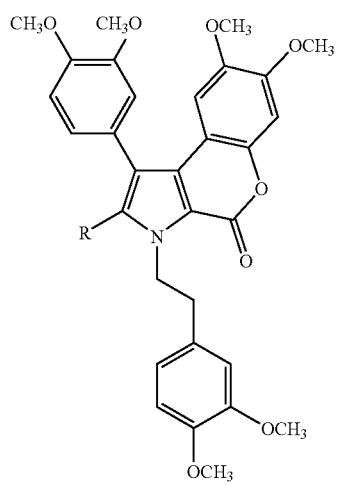
wherein R is a radical selected from the group consisting of H, CO$_2$H, CO$_2$Me and CON(Me)$_2$.
5. A compound according to claim 4 represented by the following structure:
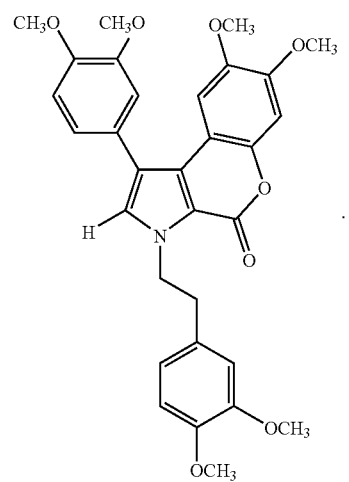
6. A compound according to claim 4 represented by the following structure:
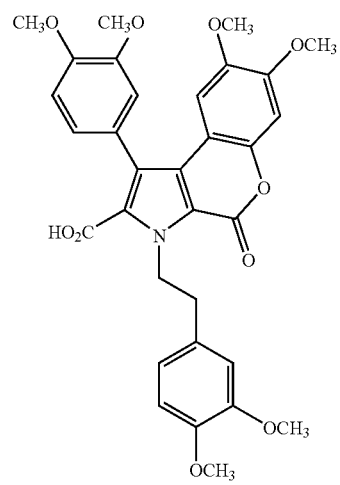
7. A compound according to claim 4 represented by the following structure:
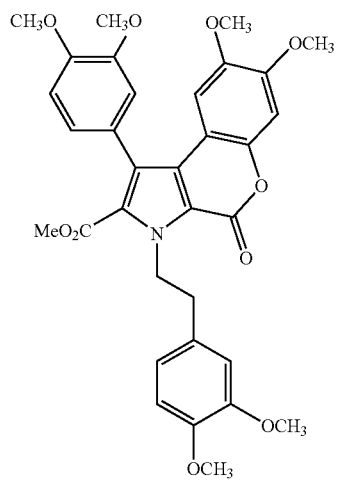

8. A compound according to claim 4 represented by the following structure:

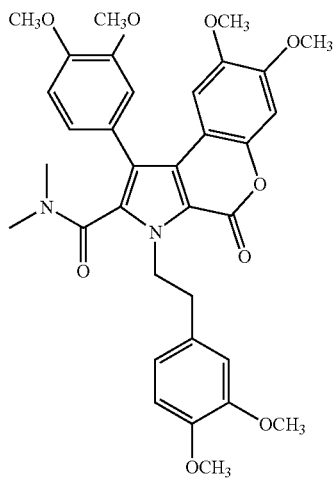

9. An analog of ningalin B represented by the following structure:

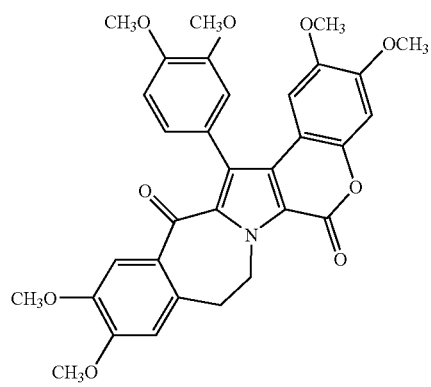

10. A synthetic process comprising the following step:

cyclizing a precursor compound with an excess of Eaton's acid at room temperature under reaction conditions for producing an analog of ningalin B, the precursor compound, the analog of ningalin B, and the cyclization reaction being represented as follows:

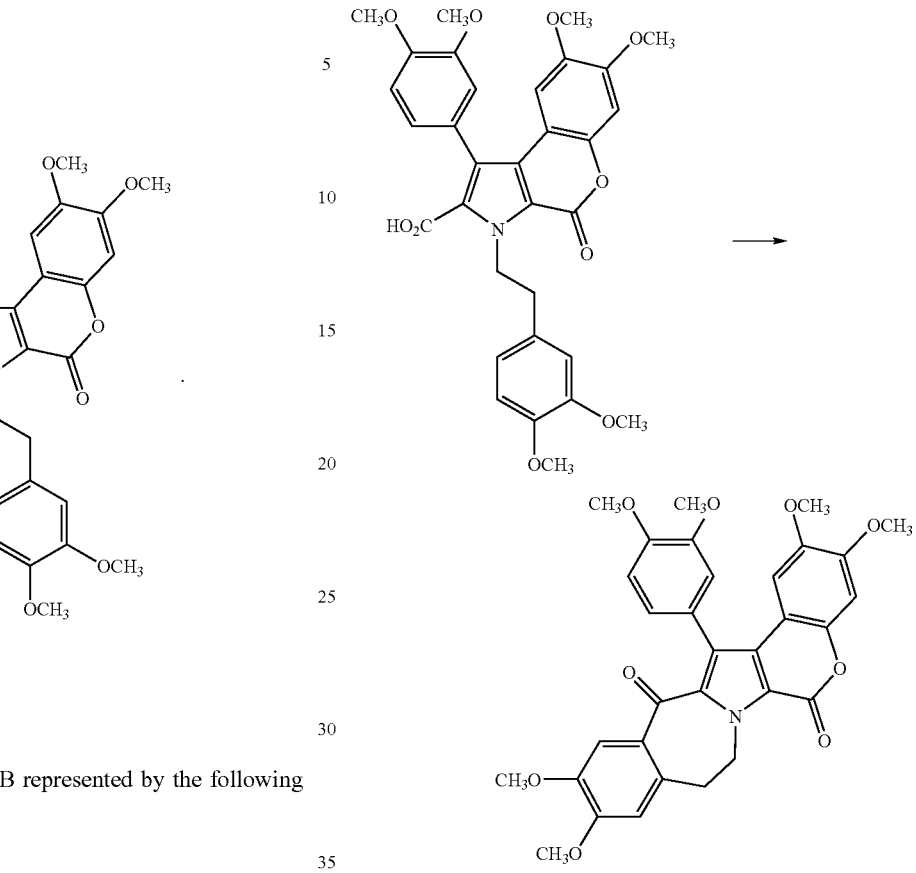

11. A process for P-gp mediated reversing multidrug resistance in a cancer cell comprising the step of contacting said cancer cell with a concentration sufficient for reversing said P-gp mediated multidrug resistance of a compound selected from a group consisting of compounds represented by the following structures:

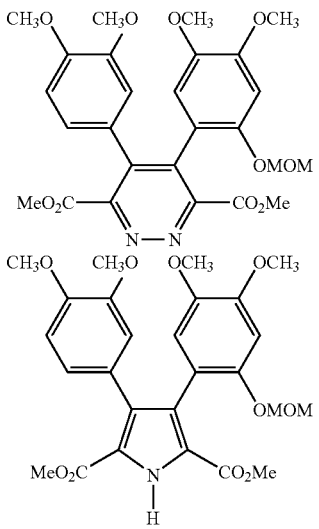

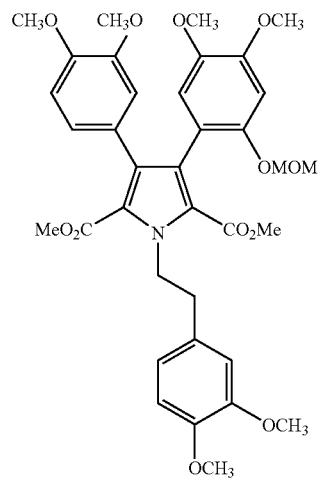
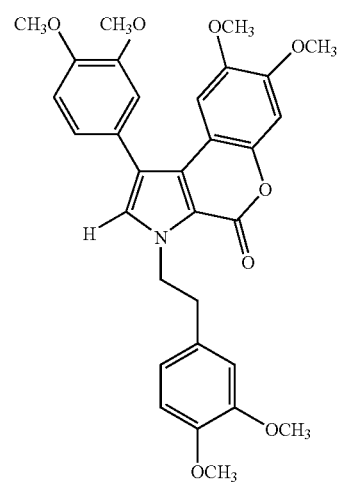
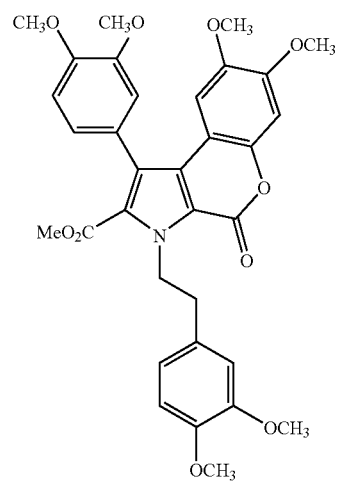
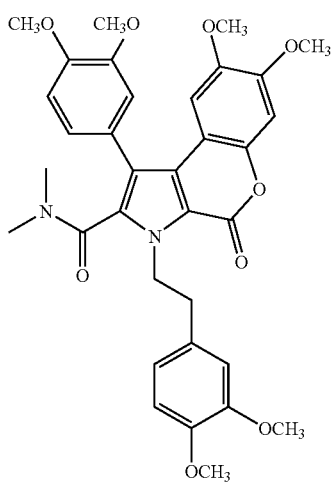
and
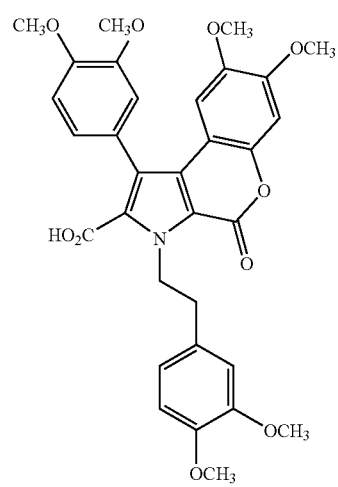
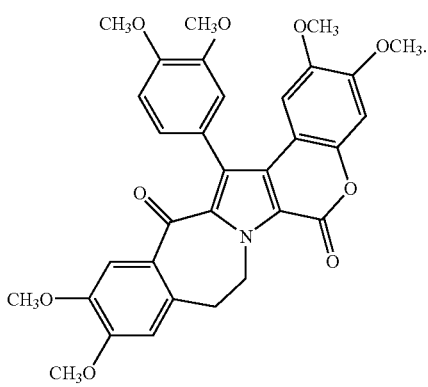

12. A process according to claim 11 wherein the compound is represented by the following structure:

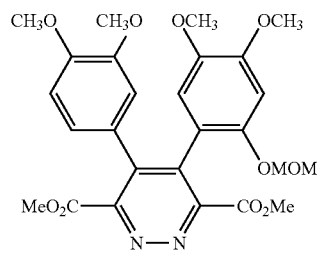

13. A process according to claim 11 wherein the compound is represented by the following structure:

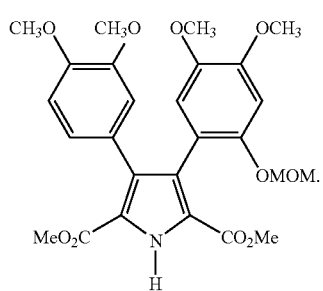

14. A process according to claim 11 wherein the compound is represented by the following structure:

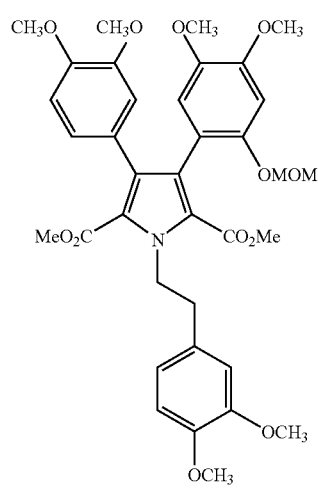

15. A process according to claim 11 wherein the compound is represented by the following structure:

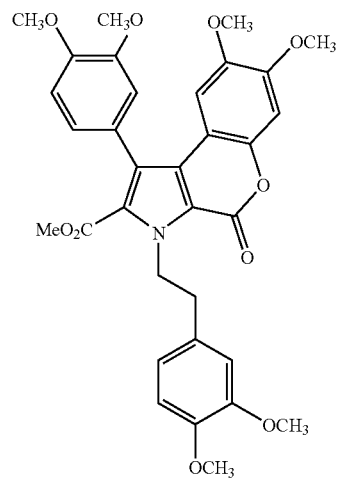

16. A process according to claim 11 wherein the compound is represented by the following structure:

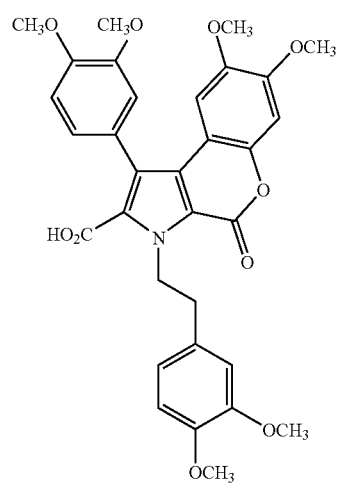

17. A process according to claim 11 wherein the compound is represented by the following structure:

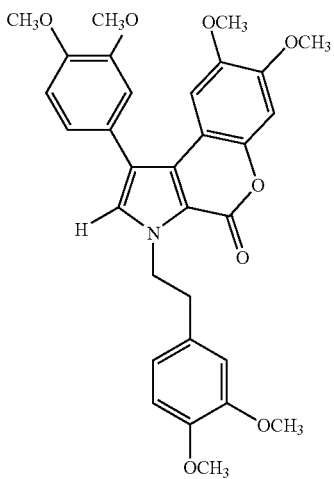

18. A process according to claim 11 wherein the compound is represented by the following structure:

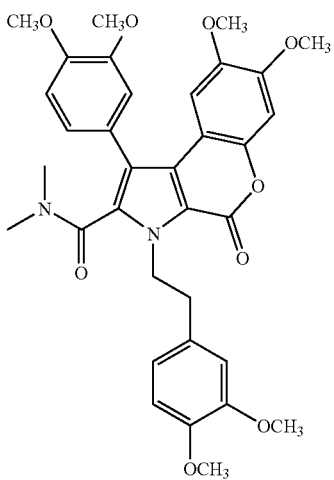

19. A process according to claim 11 wherein the compound is represented by the following structure:

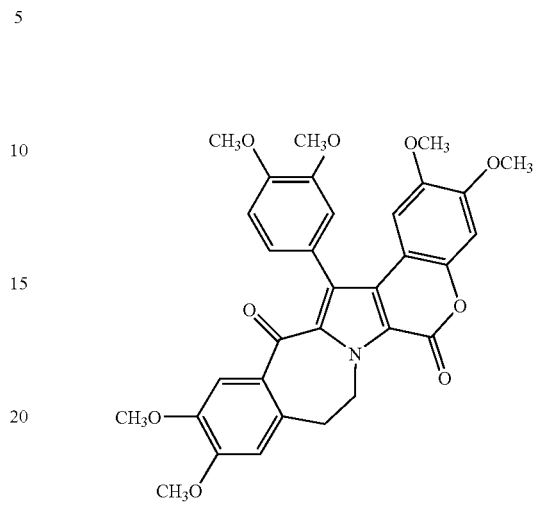

20. A solution comprising a physiological buffer suitable for injection or infusion admixed a P-gp mediated multidrug resistance reversal agent having a concentration sufficient to resensitize a cancer cell having a resistance to an anticancer drug, the multidrug resistance reversal agent being selected from any of the compounds described in claim 9.

* * * * *